United States Patent
Shahinpoor et al.

(10) Patent No.: US 6,511,508 B1
(45) Date of Patent: Jan. 28, 2003

(54) SURGICAL CORRECTION OF HUMAN EYE REFRACTIVE ERRORS BY ACTIVE COMPOSITE ARTIFICIAL MUSCLE IMPLANTS

(75) Inventors: Mohsen Shahinpoor, Albuquerque, NM (US); Parsa Shahinpoor, Albuquerque, NM (US); David Soltanpour, Larchmont, NY (US)

(73) Assignee: Environmental Robots, Inc., Albuquerque, NM (US)

( * ) Notice: Subject to any disclaimer, the term of this patent is extended or adjusted under 35 U.S.C. 154(b) by 28 days.

(21) Appl. No.: 09/633,023

(22) Filed: Aug. 4, 2000

(51) Int. Cl.[7] .................................................. A61F 2/14
(52) U.S. Cl. ........................................ 623/4.1; 600/37
(58) Field of Search ................................ 623/4.1, 6.64, 623/905, FOR 103, 14.13, 5.12; 600/37; 601/153; 607/53, 54

(56) References Cited

U.S. PATENT DOCUMENTS

| | | |
|---|---|---|
| 4,549,529 A | 10/1985 | White |
| 4,961,744 A | 10/1990 | Kilmer et al. |
| 5,147,284 A | 9/1992 | Fedorov et al. |
| 5,250,167 A | 10/1993 | Adolf et al. |
| 5,300,118 A | 4/1994 | Silvestrini et al. |
| 5,354,331 A | 10/1994 | Schachar |
| 5,389,222 A | 2/1995 | Shahinpoor |
| 5,465,737 A | 11/1995 | Schachar |
| 5,489,299 A | 2/1996 | Schachar |
| 5,503,165 A | 4/1996 | Schachar |
| 5,529,076 A | 6/1996 | Schachar |
| 5,722,952 A | 3/1998 | Schachar |
| 5,735,607 A | 4/1998 | Shahinpoor et al. |
| 5,766,171 A | 6/1998 | Silvestrini |
| 5,782,894 A | 7/1998 | Israel |
| 5,821,664 A | 10/1998 | Shahinpoor |
| 5,824,086 A | 10/1998 | Silvestrini et al. |
| 5,888,243 A | 3/1999 | Silvestrini |
| 6,006,756 A | 12/1999 | Schadduck |
| 6,007,578 A | 12/1999 | Schachar |
| 6,051,023 A | 4/2000 | Kilmer et al. |

FOREIGN PATENT DOCUMENTS

| | | | | |
|---|---|---|---|---|
| FR | 2354752 | * | 1/1978 | |
| SU | 1725875 A | * | 4/1992 | ........ 623/FOR 103 |
| WO | WO97/49354 | * | 12/1997 | ........ 623/FOR 104 |

* cited by examiner

Primary Examiner—David H. Willse
(74) Attorney, Agent, or Firm—Dennis F. Armijo

(57) ABSTRACT

Surgical correction of human eye refractive errors such as presbyopia, hyperopia, myopia, and stigmatism by using transcutaneously inductively energized artificial muscle implants to either actively change the axial length and the anterior curvatures of the eye globe. This brings the retina/macula region to coincide with the focal point. The implants use transcutaneously inductively energized scleral constrictor bands equipped with composite artificial muscle structures. The implants can induce enough accommodation of a few diopters, to correct presbyopia, hyperopia, and myopia on demand. In the preferred embodiment, the implant comprises an active sphinctering smart band to encircle the sclera, preferably implanted under the conjunctiva and under the extraocular muscles to uniformly constrict the eye globe, similar to a scleral buckle band for surgical correction of retinal detachment, to induce active temporary myopia (hyperopia) by increasing (decreasing) the active length of the globe. In another embodiment, multiple and specially designed constrictor bands can be used to enable surgeons to correct stigmatism. The composite artificial muscles are either resilient composite shaped memory alloy-silicone rubber implants in the form of endless active scleral bands, electroactive ionic polymeric artificial muscle structures, electrochemically contractile endless bands of ionic polymers such as polyacrylonitrile (PAN), thermally contractile liquid crystal elastomer artificial muscle structures, magnetically deployable structures or solenoids or other deployable structures equipped with smart materials such as preferably piezocerams, piezopolymers, electroactive and eletrostrictive polymers, magnetostrictive materials, and electro or magnetorheological materials.

21 Claims, 9 Drawing Sheets

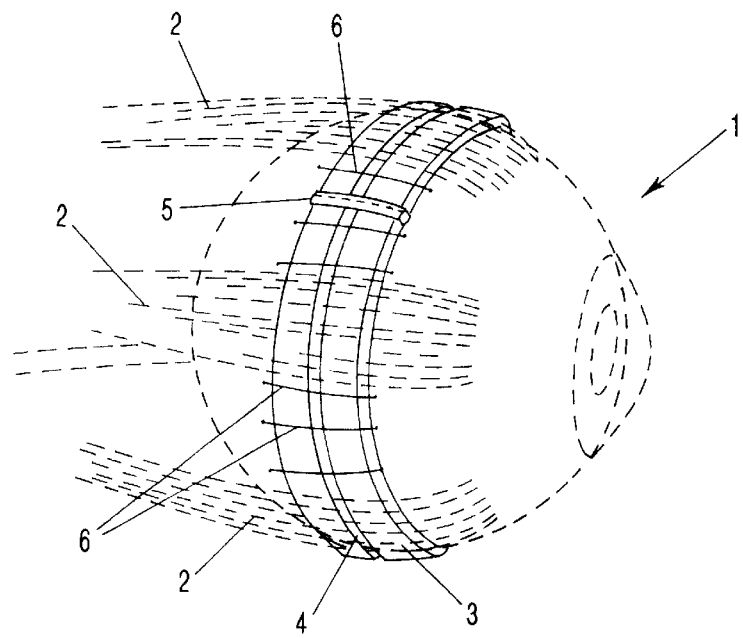
FIG-1a
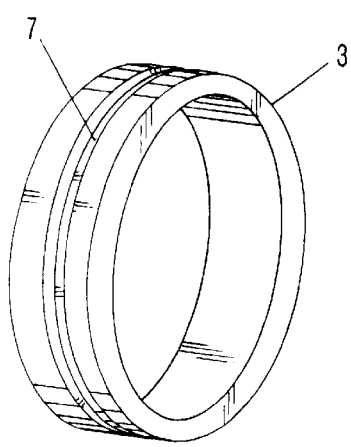
FIG-1b
FIG-1c
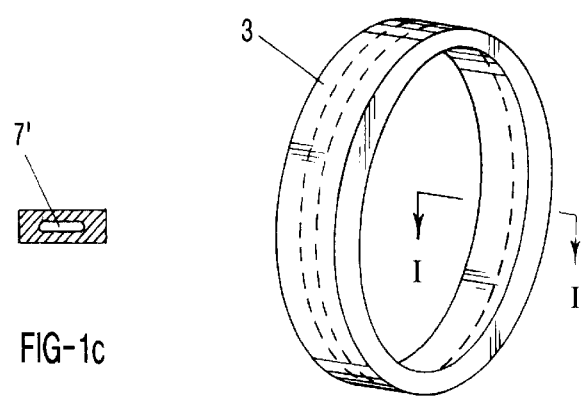
FIG-1d

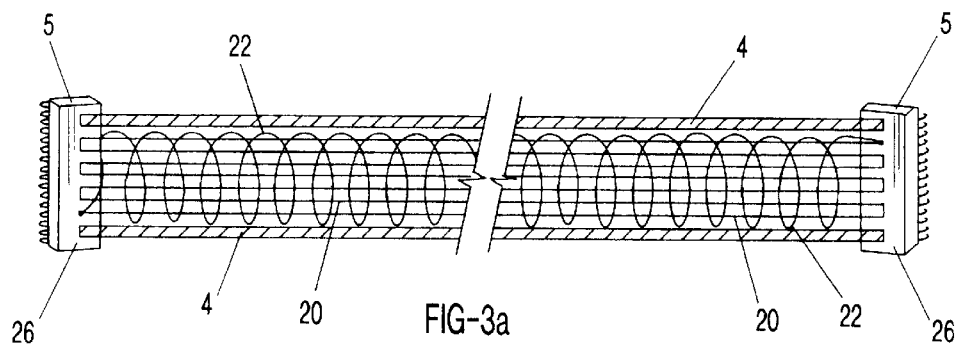
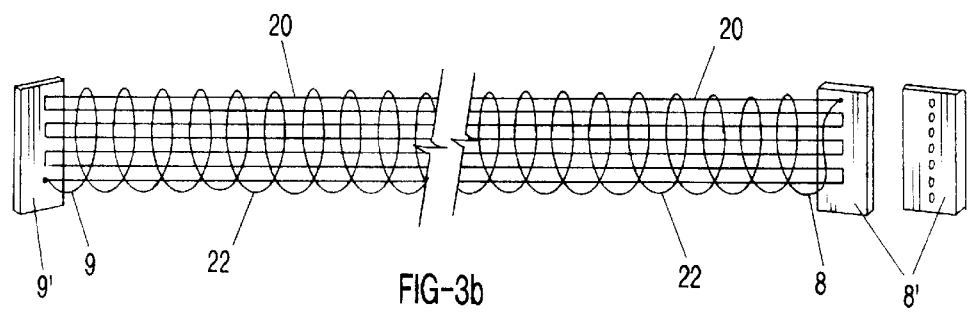
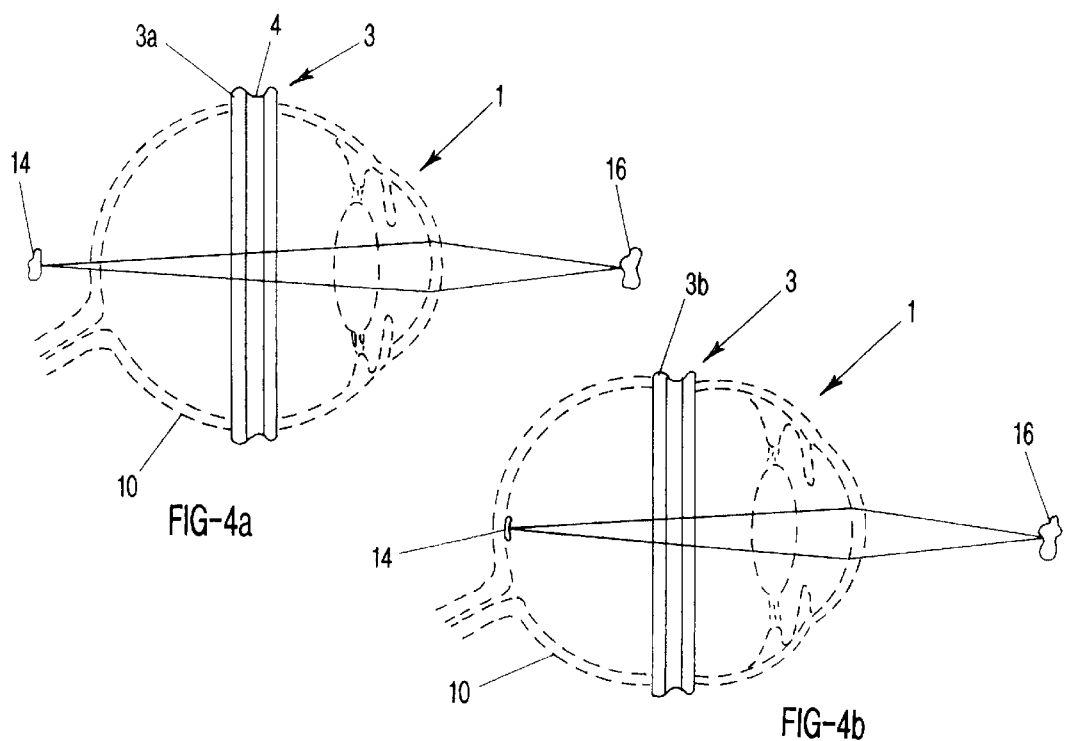

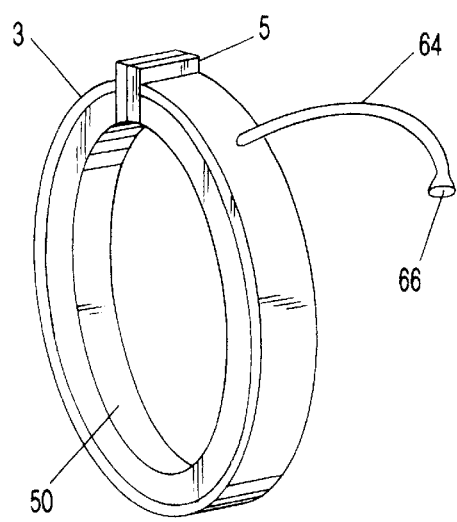
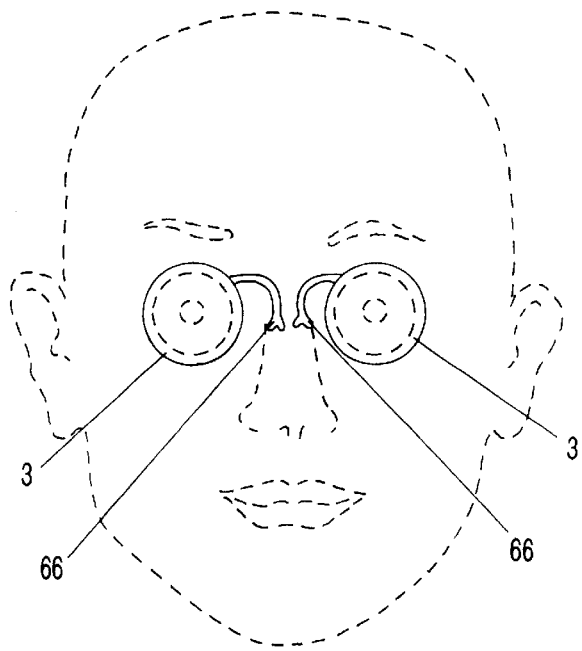
FIG-8a
FIG-8b
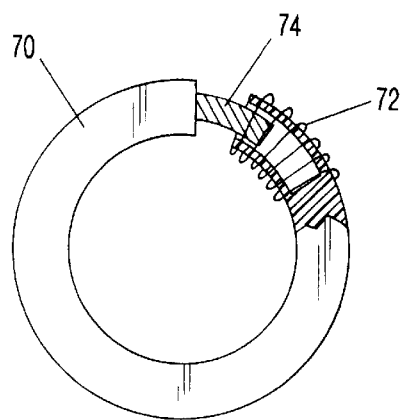
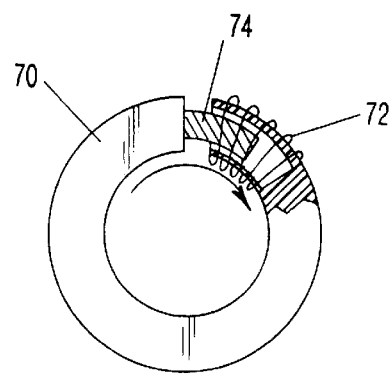
FIG-9a
FIG-9b

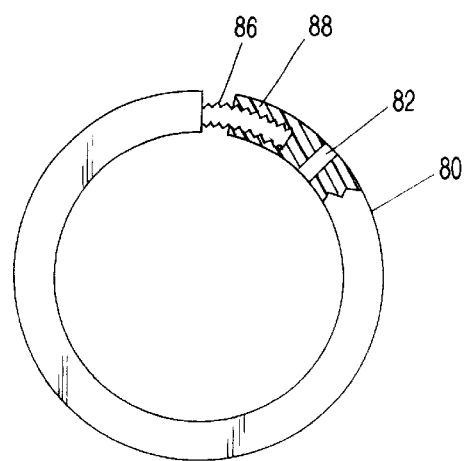 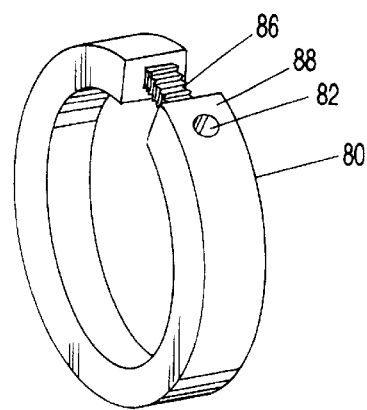
FIG-10a   FIG-10b
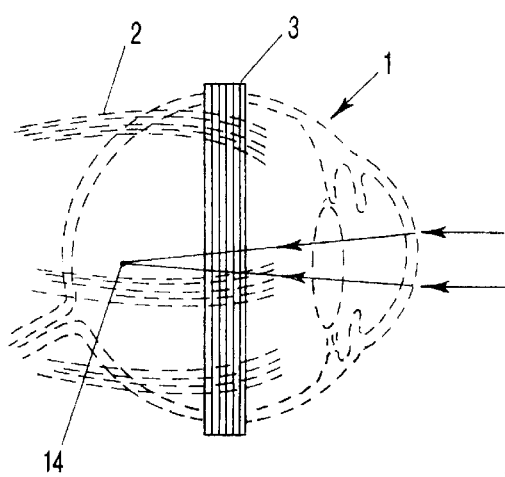 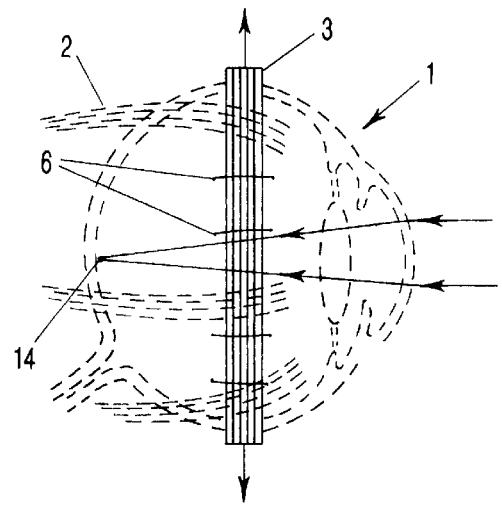
FIG-11a   FIG-11b
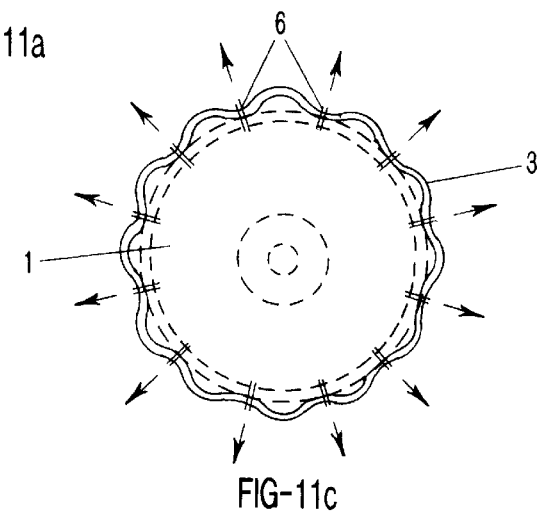
FIG-11c

SURGICAL CORRECTION OF HUMAN EYE REFRACTIVE ERRORS BY ACTIVE COMPOSITE ARTIFICIAL MUSCLE IMPLANTS

BACKGROUND OF THE INVENTION

1. Field of the Invention (Technical Field)

The invention relates to surgical correction of human eye refractive errors such as presbyopia, hyperopia, myopia, and stigmatism. More particularly, it is related to surgical corrections of such errors with implantation of a prosthesis for increasing or decreasing the eye length and scleral curvatures, and thus bringing the retina/macula region to coincide with the focal point of the eye.

2. Background Art

There are many refractive errors associated with the human eye. When the focal point of images is formed in front of the retina/macula region due to too much refraction of light rays, the refractive error is called myopia or near-sightedness. When, on the other hand, the focal point of images lie outside the eye behind the retina/macula region due to too little refraction of light rays, the refractive error is called either hyperopia or far-sightedness or presbyopia. These problems can be surgically corrected by either changing the eye length or scleral curvatures. In case of presbyopia, as individuals age, the human eye loses its ability to focus on nearby objects. This condition, known as presbyopia, is due to a progressive loss in the elasticity of the lens of the eye, such that the ciliary muscles which normally force the lens, through the action of zonule fibers on the lens capsule, in a rounded shape to accommodate near objects can no longer exert the necessary changes in the lens' shape.

The conventional optometric solution to the problems of myopia, hyperopia, and presbyopia is a prescription of glasses or reading glasses or, for individuals who already require glasses to correct other refractive errors such as myopia or astigmatism, a prescription of bifocal or multi-focal glasses.

This century has witnessed a revolution in the surgical treatment of ophthalmic disorders and refractive errors of the human eye. This revolution ranges from corneal implantations, cataract extraction, phacoemulsification of the lens, intraocular lens implantation, glaucoma implants to control the intraocular pressure, radial keratotomy, excimer laser ablation of the cornea, trabeculoplasty, iridotomy, virectomy, and the surgical buckle treatment of retinal detachment. The recent surgical solutions to myopia, hyperopia, and stigmatism have been laser photorefractive keratectomy (PRK), Lasik (laser-assisted in-situ keratomileusis) and RK or radial keratotomy. Modern techniques proposed to correct human eye refractive errors have been corneal implants (Intacs, Keravision rings, Silvestrini, intrastromal corneal ring (ICR) ) and scleral implants (SASI, Presbycorp implants, Schachar Accommodative Scleral Implants).

The effective focal length of the human eye must be adjusted to keep the image of the object focused as sharply as possible on the retina. This change in effective focal length is known as accommodation and is accomplished in the eye by varying the shape of the crystalline lens. This is necessary for the human eye to have clear vision of objects at different distances. Generally speaking, in the unaccommodated normal vision, the curvature of the lens is such that distant objects are sharply imaged on the retina. In the unaccommodated eye, close objects are not sharply focused on the retina and their images lie behind the retinal surface. In order to visualize a near object clearly, the curvature of the crystalline lens is increased, thereby increasing its refractive power and causing the image of the near object to fall on the retina. The change in shape of the crystalline lens is accomplished by the action of ciliary muscle by which the radial tension in the lens is reduced, according to classical Helmholtz theory of accommodation, and it becomes more convex. Based on Helmholtz theory, in the unaccommodated human eye the lens and its capsule are suspended on the optical axis behind the pupil by a circular assembly of many radially directed collagenous fibers, the zonules, which are attached at their inner ends to the lens capsule and at their outer ends to the ciliary body, a muscular constricting ring of tissue located just within the outer supporting structure of the eye, the sclera. The ciliary muscle is relaxed in the unaccommodated eye and therefore assumes its largest diameter. According to the Helmholtz classical theory of accommodation, the relatively large diameter of the ciliary body in this unaccommodated condition, causes a tension on the zonules which in turn pull radially outward on the lens capsule, making it less convex. In this state, the refractive power of the lens is relatively low and the eye is focused for clear vision of distant objects. When the eye is intended to be focused on a near object, the muscles of the ciliary body contract. This contraction causes the ciliary body to move forward and inward, thereby relaxing the outward pull of the zonules on the equator of the lens capsule and reducing the zonular tension on the lens. This allows the elastic capsule of the lens to contract causing an increase in the sphericity of the lens, resulting in an increase in the optical refraction power of the lens. Recently, Schachar (whose inventions are discussed below) has proposed a radically different theory of accommodation which refutes the Helmholtz theory.

Accordingly, the present invention relates to systems and methods of compensating presbyopia, hyperopia, myopia, and stigmatism by actively changing the length of the eye globe in the direction of optical axis or its curvature, on demand, using active constricting (sphinctering) artificial muscles as active scleral bands. The scleral band in the form of an active and smart constricting/expanding band comprising an active prosthesis which can be remotely powered by small inductive generators that can be placed near the eye, preferably behind the ears or under the skin on the shoulder or on an arm band.

There are several prior art devices and methods in the form of implants and prostheses for the surgical correction of presbyopia, hyperopia, and myopia.

U.S. Pat. No. 5,354,331 to Schachar, discloses how presbyopia and hyperopia are treated by a method that increases the amplitude of accommodation by increasing the effective working distance of the ciliary muscle in the presbyopic eye. This is accomplished by expanding the sclera in the region of the ciliary body. A relatively rigid band having a diameter slightly greater than that of the sclera in that region is sutured to the sclera in the region of the ciliary body. The scleral expansion band comprises anterior and posterior rims and a web extending between the rims, the anterior rim having a smaller diameter than the posterior rim.

In U.S. Pat. No. 5,465,737 to Schachar, the teachings are similar to those of the '331 patent, except that by weakening the sclera overlying the ciliary body, by surgical procedures or treatment with enzymes, heat or radiation, whereby intraocular pressure expands the weakened sclera, or by surgical alloplasty. The effective working distance of the ciliary muscle can also be increased by shortening the zonules by application of heat or radiation, by repositioning one or both insertions of the ciliary muscle or by shortening the ciliary muscle. Presbyopia is also arrested according to the invention by inhibiting the continued growth of the crystalline lens by application of heat, radiation or antimitotic drugs to the epithelium of the lens. Primary open angle glaucoma and/or ocular hypertension can be prevented and/or treated by increasing the effective working range of the ciliary muscle according to the invention.

U.S. Pat. Nos. 5,489,299; 5,722,952; 5,503,165; and 5,529,076 to Schachar contain essentially the same ideas as U.S. Pat. Nos. 5,354,331 and 5,465,737 with some improvements such that presbyopia and hyperopia are treated by a method that increases the amplitude of accommodation by increasing the effective working distance of the ciliary muscle in the presbyopic eye. The effective working distance of the ciliary muscle is increased by shortening the zonules by application of heat or radiation, by repositioning one or both insertions of the ciliary muscle or by shortening the ciliary muscle. Presbyopia is also arrested by inhibiting the continued growth of the crystalline lens by application of heat, radiation or antimitotic drugs to the epithelium of the lens. Primary open angle glaucoma and/or ocular hypertension can be prevented and/or treated by increasing the effective working range of the ciliary muscle.

U.S. Pat. No. 6,007,578 to Schachar, discloses how presbyopia is treated by implanting within a plurality of elongated pockets formed in the tissue of the sclera of the eye, transverse to a meridian of the eye, a prosthesis having an elongated base member having an inward surface adapted to be placed against the inward wall of the pocket and having a ridge on the inward surface of the base extending along at least a major portion of the major dimension of the base. The combined effect of the implanted prostheses is to exert a radially outward traction on the sclera in the region overlying the ciliary body which expands the sclera in the affected region together with the underlying ciliary body. This restores the effective working distance of the ciliary muscle in the presbyopic eye and thereby increases the amplitude of accommodation. Hyperopia, primary open angle glaucoma and/or ocular hypertension can be treated by increasing the effective working distance of the ciliary muscle.

U.S. Pat. No. 6,006,756 to Shadduck, discloses a system and technique called magnetoresonant induction of an intrastromal implant that is adapted for corneal re-shaping. The technique is utilized to correct mild to high hyperopia and presbyopia by steepening the anterior corneal curvature in a single treatment, or in periodic treatments over the lifetime of the patient. The system comprises a combination of components including (i) at least one implantable magnetoresonant intrastromal segment, and (ii) an oscillating magnetic field generator together with a dosimetry control system including at least one emitter body adapted for positioning proximate to the patient's eye and intrastromal implant. The system can deliver thermal effects to appropriate stromal lamellae by non-contact inductive heating of the implant which in turn contracts or compresses stromal collagen fibrils into a circumferential cinch about an anterior layer of the cornea and steepens the anterior corneal curvature. A dosimetry control system controls the power level and duration of exposure of the oscillating magnetic field(s) and may be combined with intraoperative corneal topography.

U.S. Pat. No. 5,147,284 to Fedorov, et al, teaches a device for restoration of visual functions in cases of affected optic nerve and retina with an electromagnetic field radiator emitting the latter field into the region of the eyeball and an electromagnetic field receiver adapted to interact with the radiator. Both of these exert an electrostimulation effect on the optic nerve and the retina. The electromagnetic field radiator is a source of a pulsed magnetic field and is shaped as an electromagnet provided with an adjuster of a distance between the end of the electromagnet and the electromagnetic field receiver, which is in effect an inductor having lead wires furnished with electrodes whose active surface exceeds 10 mm2. A method for restoration of visual functions in cases of affected optic nerve and retina consists in conducting electrostimulation of the eyeball, for which purpose an inductor is implanted into the orbit on the sclera of the posterior portion of the eyeball in such a manner that one of the inductor electrodes is positioned nearby the external tunic of the optic nerve, while the other electrode is fixed on the sclera in the area of the eyeball equator, whereupon a pulsed magnetic flux is applied remotely to the eyeball portion carrying the inductor, the magnetic field induction being from 0.1 T to 0.25 T, while the pulsed magnetic field is simultaneously brought in synchronism with pulsation of the internal carotid artery.

U.S. Pat. No. 5,782,894 to Israel, discloses a device and method for treating presbyopia by which the ciliary muscles of the eyes are electrically stimulated when the internal rectus muscles of the eyes are activated in order to focus the eyes on objects within the near field of vision. The amounts of electrical stimulation can be adjusted according to the individual needs of a patient and are preferably in direct proportion to the amounts of contraction of the internal muscles.

U.S. Pat. No. 4,961,744 to Kilmer, et al, discloses a surgical apparatus for inserting a plastic, split end, adjusting ring into the stroma of the cornea of the eye wherein the adjusting ring includes, as a part thereof, a dissecting head to part the stroma and provide a pathway for the adjusting ring as the ring is rotated. The ends of the adjusting ring are moved to change the shape of the cornea to a desired shape in accordance with the desired visual correction after which the ends of the adjusting ring are fixably joined to maintain the desired shape.

U.S. Pat. No. 5,300,118 to Silvestrini, et al, discloses an intrastromal corneal ring (ICR) that is adjustable in thickness and has an elongated, flexible, preferably transparent or translucent body which forms a circle. The ICR is of a size such that it can be inserted into a human eye and is comprised of a material which is compatible with human ocular tissue. The thickness of the ring can be adjusted so that it is not necessary to stock a plurality of different rings of different sizes to be used in connection with a method of adjusting the shape of the cornea of the eye. A plurality of different embodiments of ICRs are disclosed each of which are adjustable in terms of their thickness. The thickness may be adjusted prior to the insertion of the ICR into the cornea and may not be further adjustable after insertion. However, in accordance with preferred embodiments, the ICR is inserted at a thickness which is believed to be proper and may thereafter be further adjusted in order to precisely define the desired thickness and thereby more precisely adjust the shape of the cornea, and focus the light entering the eye on the retina.

U.S. Pat. No. 5,824,086 to Silvestrini, discloses a preformed intrastromal corneal insert. It is made of a physiologically compatible polymer and may be used to adjust corneal curvature and thereby correct vision abnormalities. The insert or segment may also be used to deliver therapeutic or diagnostic agents to the interior of the cornea or of the eye. The insert subtends only a portion of a ring or "arc" encircling the anterior cornea outside of the cornea's field of view. The invention also includes a procedure for inserting the device into the cornea.

U.S. Pat. No. 6,051,023 to Kilmer, et al, discloses a surgical apparatus for inserting a plastic, split end, adjusting ring into the stroma of the cornea of the eye wherein the adjusting ring includes, as a part thereof, a dissecting head to part the stroma and provide a pathway for the adjusting ring as the ring is rotated. The ends of the adjusting ring are moved to change the shape of the cornea to a desired shape in accordance with the desired visual correction after which the ends of the adjusting ring are fixably joined to maintain the desired shape.

U.S. Pat. No. 5,888,243 to Silverstrini, discloses an intrastromal corneal ring housing comprising at least one outer layer of a physiologically compatible polymer having a low modulus of elasticity, which polymer may be hydratable and may be hydrophilic. The inner portion of the hybrid intrastromal corneal ring may be hollow or may contain one or more physiologically compatible polymers.

U.S. Pat. No. 5,766,171 to Silvestrini, teaches a device and procedure for the correction of optical abnormalities in a human eye. It involves use of an inventive electrosurgical energy probe with specific physical configurations. The process preferably utilizes a high frequency RF electro-desiccation or ablation device. The procedure involves the initial step of forming at least one access site allowing access to the corneal volume behind the Bowman's Layer. It is placed in the anterior surface of the cornea through and ending posterior to the Bowman's layer of the eye. The electrosurgical probe is then introduced into the access site, and depending upon the visual abnormality to be corrected, the probe is activated to adjust the volume of the corneal stromal layers through ablation or desiccation. The shape of the volume desiccated or ablated is dependent upon the aberration to be corrected. In other instances, such as for the treatment of astigmatism, certain smaller sections of the corneal volume may be shrunk. In certain circumstances, the Bowman's layer may be cut to allow the curvature of the cornea to change after the corneal volume adjustment. These relief cuts may be radial, circular, semicircular or any other form appropriate for the option adjustment needed.

SUMMARY OF THE INVENTION
(DISCLOSURE OF THE INVENTION)

The invention disclosed is an apparatus and method to create on-demand correction of refractory errors in the eye by the use of an active and smart scleral band equipped with composite artificial muscles. The scleral band induces scleral constriction or expansion, similar to a scleral buckle in retinal detachment surgical correction. The scleral band is an encircling composite silicon band around the middle of the eye's globe to provide relief of intraretinal tractional forces by indentation of the sclera as well as repositioning of the retina and choroid. It can also induce myopia, depending on how much tension is placed on the buckle, by increasing the length of the eye globe in the direction of optical axis. By using the scleral band, one can actively change the axial length of the scleral globe in order to induce refractive error correction. For example, inducing a slight degree of myopia, one to three diopters has been shown to enable presbyopes to read without the use of glasses.

The present invention creates an active smart band to encircle the sclera, which constricts or expands in such a way to induce temporary myopia or hyperopia. The smart band is implanted under the conjunctiva, preferably under the extraocular muscles. This band is secured to the sclera in a similar manner used in scleral buckle surgery. The smart band is either a singular or composite contractile artificial muscle which will be transcutaneously inductively heated to raise its temperature to a critical value (about 40 degrees Celsius) at which the smart muscle band will resiliently contract, preferably up to 6% or more. This will create a mild scleral constriction which will in turn cause the length of the eye to increase, and the retina/macula region to move back to coincide with the focal point of the image of a near object, to accommodate presbyopia, and hyperopia by inducing a temporary mild myopia, thus correcting the presbyopic vision. The scleral band preferably comprises an interior body of contractile Shape-Memory Alloy (SMA) actuator wires or ribbons with attachable ends to make an endless band encased or embedded inside a silicone rubber sheath or cladding. The rubber cladding acts as a resilient structure to store potential energy when the SMA wires or ribbons contract and use the stored resilient (springy) potential energy to stretch the contractile wires or ribbons back to their initial relaxed length when the wires or ribbons cool off and expand. This also helps relax the sclera back to its initial dimensions when the temperature is reverted back to the normal body temperature. The SMA wires or ribbons go through a solid Martensite-Austenite phase transformation during their contraction, i.e., as they are transcutaneously inductively heated, at the critical Austenite start temperature, for example 40 degrees Celsius. The wires contract and create enough constricting force to compress the silicone rubber cladding thus buckling the sclera. This creates an indentation of the sclera which causes the eye to lengthen and thus presbyopia or hyperopia are accommodated. By turning the remote inductive heating generators off, the temperature of the smart band reverts back to normal or Martensite finish temperature. The SMA wires or ribbons make a solid phase transformation to Martensite phase, thus, enabling the silicone rubber cladding resilient unbuckling force to stretch the wires or ribbons back to their normal stress-free state. This will induce Emmetropia ("normal" vision). Another embodiment of the smart scleral band is an armature winding made with gold ribbons to act as an inductive heating coil to heat up the SMA wires. The inductive generators (battery-operated magneto-resonant coils) can be housed behind the ears of the person wearing the scleral prosthesis, worn like an arm band or surgically implanted under the skin in an easily accessible location and preferably can be tuned on or off by the person wearing them by a touch of a finger (on-demand virtual reading glasses).

Other alternative embodiments are scleral constricting bands equipped with other types of composite artificial muscles such as resilient composite shape memory alloy-silicone rubber implants in the form of endless active scleral bands, electroactive ionic polymeric artificial muscle structures, electrochemically contractile endless bands of ionic polymers such as polyacrylonitrile (PAN), thermally contractile liquid crystal elastomer artificial muscle structures, magnetically deployable structures or other deployable structures equipped with smart materials such as piezocerams, piezopolymers, electroactive and electrostrictive polymers, magnetostrictive materials, and electro or magnetorheological materials.

To install the scleral band the following surgical procedure is performed. A 360-degree conjunctiva peritomy is performed. The conjunctiva is carefully dissected free from the sclera. Each of the extraocular muscles are isolated and freed from the check ligaments. The composite artificial muscle constricting band is then placed underneath the extraocular muscles and then secured together creating a 360 degree band encircling the sclera. The band is then secured to the sclera using 6.0 nylon sutures, or the like. In the alternative, the artificial muscle band can be placed 3 mm from the sclera and the band implanted one half thickness into the sclera. The simplest method of implantation is similar to the method used for scleral buckle surgery. The two alternative positions will increase the axial length and local curvature of the globe. The composite artificial muscle will deactivate on command returning the axial length to its original position and vision back to normal (emmetropic vision).

A primary object of the present invention is to create on-demand correction of refractory errors in the eye by the use of an active and smart (computer-controllable) scleral band equipped with composite artificial muscles.

Another object of the present invention to create an active smart band to encircle the sclera, which will constrict or expand in such a way to induce temporary myopia or hyperopia.

A primary advantage of the present invention is that the installation of the present invention on a human eye does not include destructive intervention like the present implantable devices or laser correctional surgery such as RK, PRK or Lasik.

Another advantage of the present invention is that this will be an active and smart mechanism to be implemented when one is reading.

Other objects, advantages and novel features, and further scope of applicability of the present invention will be set forth in part in the detailed description to follow, taken in conjunction with the accompanying drawings, and in part will become apparent to those skilled in the art upon examination of the following, or may be learned by practice of the invention. The objects and advantages of the invention may be realized and attained by means of the instrumentalities and combinations particularly pointed out in the appended claims.

BRIEF DESCRIPTION OF THE DRAWINGS

The accompanying drawings, which are incorporated into and form a part of the specification, illustrate several embodiments of the present invention, and together with the description, serve to explain the principles of the invention. The drawings are only for the purpose of illustrating a preferred embodiment of the invention and are not to be construed as limiting the invention. In the drawings:

FIG. 1(a) is an isometric view of the present invention surgically mounted on the scleral globe under the extraocular muscles and sutured to the anterior surface of the sclera;

FIG. 1(b) is a scleral buckle tire with an annular groove used to create a cushion between the active scleral constricting band placed in the annular groove of the tire and the scleral anterior surface;

FIG. 1(c) is a cross section view of FIG. 1(b);

FIG. 1(d) is a scleral buckle tire with an annular tunnel used to create a cushion between the active scleral constricting band placed in the annular tunnel of the tire and the scleral anterior surface;

FIG. 3(a) shows another rendition of FIG. 2(a) in an open configuration;

FIG. 3(b) shows another rendition of FIG. 2(b) in an open configuration;

FIG. 4(a) shows the invention of FIG. 1 around the outside surface of the sclera sutured and fixated under the extraocular muscles of the eye in a relaxed inactivated state;

FIG. 4(b) shows the invention of FIG. 4(a) in an activated state causing the sclera to buckle and the eye length to increase;

FIG. 8(a) is an isometric view of another alternate embodiment of the invention equipped with an inextensible support band and an inflatable bladder skirt;

FIG. 8(b) shows the embodiment of FIG. 8(a) attached to a users nose;

FIG. 9(a) depicts another embodiment of the present invention in which the constricting action is obtained by an endless solenoid or coil gun configuration in an expanded configuration;

FIG. 9(b) depicts the embodiment of FIG. 9(a) in a constricting configuration;

FIG. 10(a) shows a side view of another embodiment of the invention wherein the band is comprised of a bio-compatible resilient polymer;

FIG. 10(b) shows an isometric view of FIG. 10(a) and yet another embodiment of the active scleral band of this invention wherein the band is comprised of a bio-compatible resilient polymer;

FIG. 11(a) shows an isometric view of another embodiment of the invention in initial stage of operation as a scleral expansion band to shorten the eye length to correct myopia;

FIG. 11(b) shows an isometric view of FIG. 11(a) in an active expanded configuration;

FIG. 11(c) shows a side view of the embodiment of FIG. 11(b);

DESCRIPTION OF THE PREFERRED EMBODIMENTS (BEST MODES FOR CARRYING OUT THE INVENTION)

This invention creates on-demand temporary change in eye length by the use of a band assembly that constricts the sclera on demand. The invention employs composite artificial muscles in an implant or prosthesis to surgically correct presbyopia, hyperopia, and myopia, on demand (virtual reading glasses). For example, this invention can induce temporary mild myopia, one to three diopters, which has been shown to enable presbyopes to read without the use of glasses in order to correct presbyopia, hyperopia, and myopia. The invention creates an active sphinctering smart band to encircle the sclera, implanted under the conjunctiva, preferably under the extraocular muscles which will expand or constrict, similar to a scleral buckle surgery. This increases or decreases the active length of the globe and thus corrects presbyopia, hyperopia, and myopia on demand.

Figure 1E:
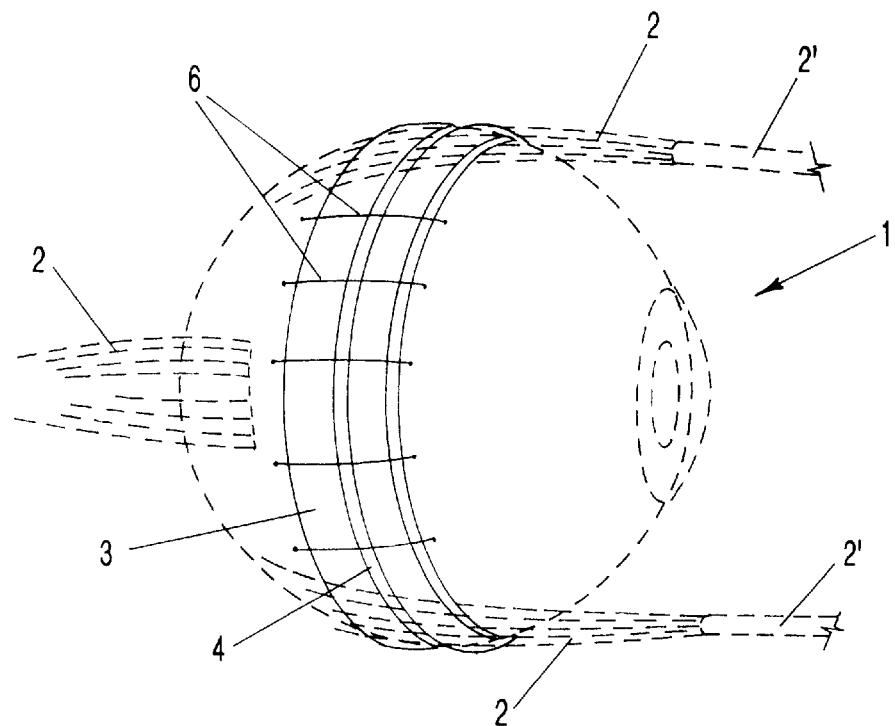
FIG. 1(e) is a cut out view of FIG. 1(a) showing the configuration of the tire 3 and the active scleral constrictive band 4 placed in the groove 7 of the tire.
Figure 1F:
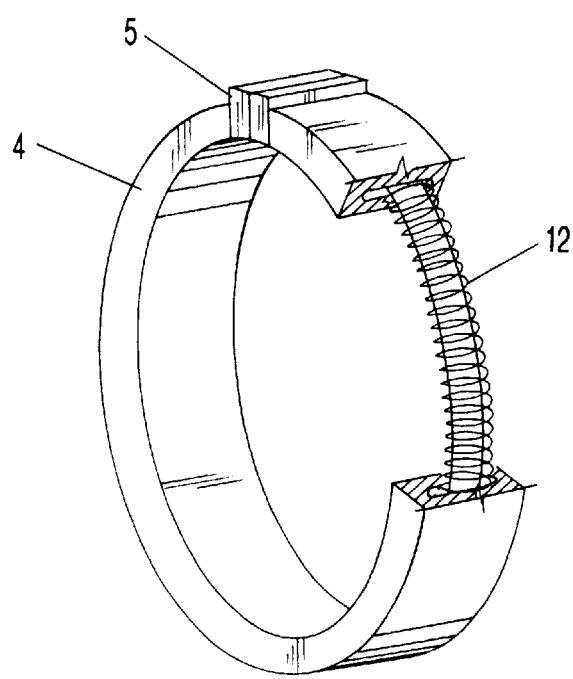
FIG. 1(f) is a transparent rendition of the active scleral constrictive band composed of embedded artificial muscle wire induction coil assembly 12, embedded inside a silicone rubber cladding 4 with snappable ends 5.

FIGS. 1(a, b, c, d, e, and f) show an isometric view of the composite scleral tire 3, composite artificial muscle active scleral band 4, surgically mounted on the scleral globe 1 under the extraocular muscles 2 and mattress sutured 6 to the anterior surface of the sclera 10. Artificial muscle assembly 12 is embedded inside silicone cladding 4 with snappable ends 5 to be placed inside the groove 7 or the tunnel 7' of scleral tire 3. The surgical procedure is such that the artificial muscle assembly 12 embedded inside silicone cladding 4, in the form of a band will be placed inside the central groove 7 or tunnel 7' of the scleral buckle surgery tire 3 in a relaxed and stress free state. The tire/muscle assembly or smart band 3 is then surgically placed equatorially around the scleral globe 1, similar to well known scleral buckle surgery, and mattress sutured 6 to the scleral globe 1.

The operation of the smart band 3 is such that upon transcutaneous inductive heating of the endless artificial assembly SMA wire inductive coil assembly 12, embedded inside the silicone cladding 4 and placed in the scleral tire assembly 3, to the artificial muscle activation temperature or the Austenite start temperature, for instance 40 degrees Celsius, the SMA band 12 contracts to a smaller diameter and thus exerts a constricting or squeezing circularly distributed force or pressure on the silicone cladding 4 as well as the scleral tire 3, which in turn transmits that distributed annular force to the sclera causing the eye or scleral globe 1 to lengthen. This will bring the retina/macula region to coincide with the focal point of the eye and thus correct presbyopia as shown in FIG. 4(b). SMA actuators such as described in U.S. Pat. No. 5,735,607 to Shahinpoor and U.S. Pat. No. 5,821,664 to Shahinpoor can be used, as well as similar actuators that are well known in the art.

Figure 2A:
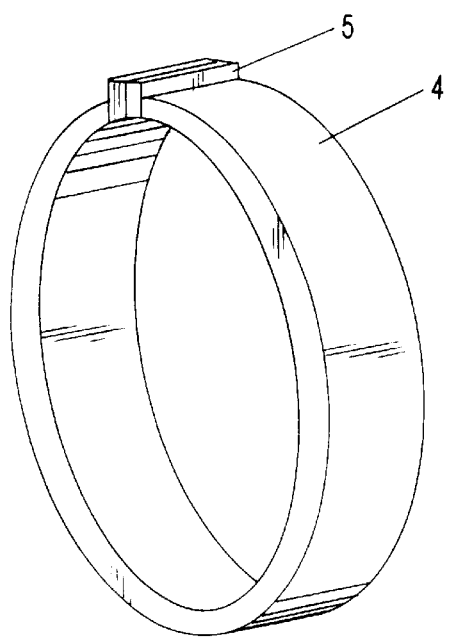
FIG. 2(a) shows an exploded view of the invention of FIG. 1 with silicone cladding.
Figure 2B:
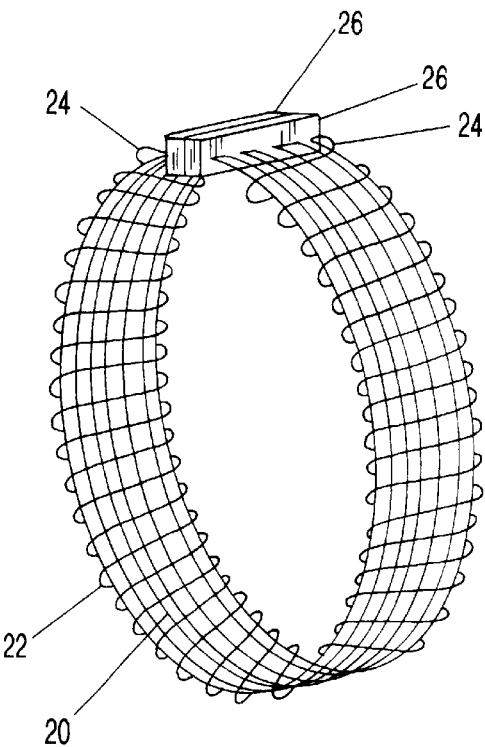
FIG. 2(b) is another exploded view of FIG. 1 showing the embedded SMA wires (ribbons) and the induction coil wrapped around the SMA wires (ribbons)
Figure 2C:
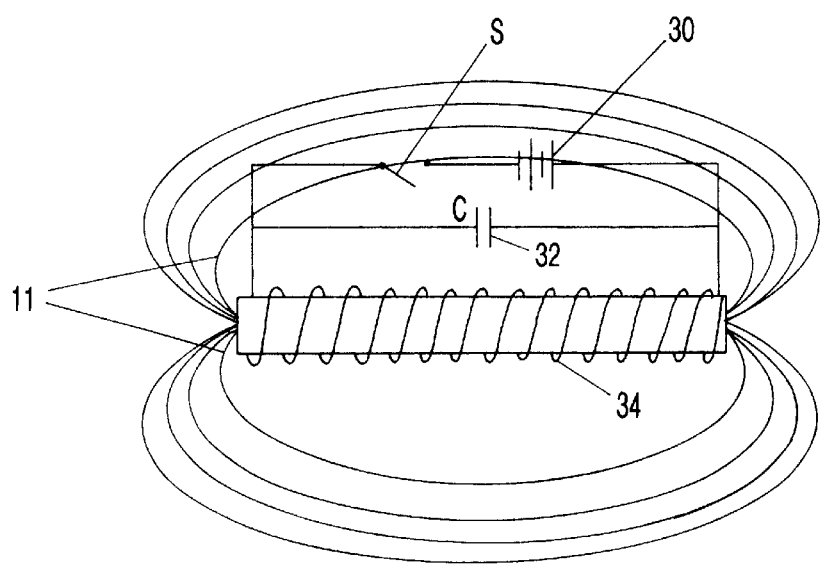
FIG. 2(c) shows the induction generator powered by a source and stabilized by a capacitor creating the induction flux lines to induce a current in the induction coil of FIG. 2(b)

FIGS. 2(a), 2(b), and 2(c) show an exploded view of the composite SMA-Silicone artificial muscle active scleral band 12 of FIG. 1. FIG. 2(a) shows the scleral band 12 with silicone cladding 4 and snappable ends 5. FIG. 2(b) shows the embedded SMA wires (ribbons) 20 and the induction coil 22 wrapped around the SMA wires (ribbons) 20. The ends of the SMA wires (ribbons) 24 are connected to end fixtures 26 by bonding or other well known affixing means. End fixtures 26 can snap or bond together by standard means such as sutures, magnets, Velcro®, or the like. FIG. 2(c) shows the induction generator 34 powered by a battery source E 30 and stabilized by a capacitor C 32, thereby creating the induction flux lines 11 to induce a current in induction coil 22 of FIG. 2(b). Thus, one can remotely energize (heat) the SMA wires (ribbons) 20 to an Austenite start temperature of about 40 degrees Celsius, to cause SMA wires 20 to contract and thus causing the scleral tire 3 to uniformly and circularly constrict the sclera to cause an increase in the eye length and thus, correct presbyopia and accommodate near object vision.

FIG. 3 shows another rendition of FIGS. 2(a) and 2(b) in an open configuration. Silicone cladding 4 houses the SMA wires (ribbons) 20 which are wrapped by means of an induction coil 22. The SMA wires 20 are attached to end fixtures 26 with holes through which the SMA wires 20 are serpentined and zigzagged and eventually connected to pins 8' and 9' by means of end connector wires 8 and 9. The assembly of SMA wires 20, end fixtures 26 and induction coil 22, are embedded in silicone cladding 4 which are attached to end fixtures 26. End fixtures 26 can have snappable ends 5 which may preferably snap or bond together by standard means such as sutures, magnets, Velcro®, or the like.

FIG. 4(a) shows the composite scleral tire 3 with a SMA-Silicone cladding 4 of FIG. 1, around the outside surface of the sclera 10 of the eye in a relaxed inactivated state. FIG. 4(b) shows the invention in an activated state causing the sclera 10 to buckle and the eye length to increase. The operation of the tire assembly 3 with silicone cladding 4 is such that upon transcutaneous inductive heating of the endless SMA band, to the Austenite start temperature, the tire assembly 3 with silicone cladding 4 contracts to a smaller diameter as shown in FIG. 4(b), and thus exerts a constricting or squeezing circularly distributed force or pressure equatorially on the scleral tire which in turn transmits that distributed annular force to the sclera causing the eye to lengthen. This will bring the retina/macula region to coincide with the focal point 14 of the eye for viewing an object 16 and thus correct presbyopia.

Figure 5C:
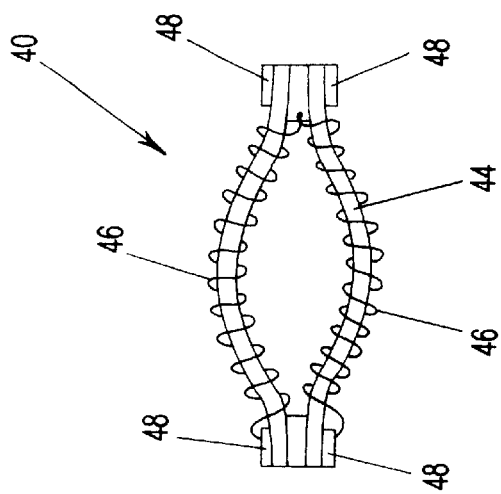
FIG. 5(c) shows the ionic polymer active by-strips of FIG. 5(a) with induction coils.
Figure 5B:
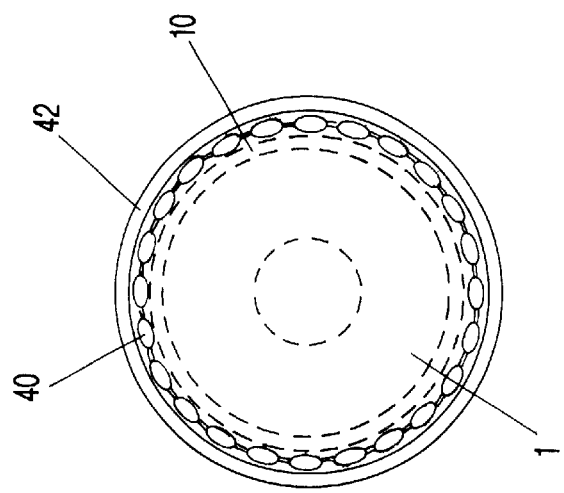
FIG. 5(b) is a front view of the embodiment of FIG. 5(a)
Figure 5A:
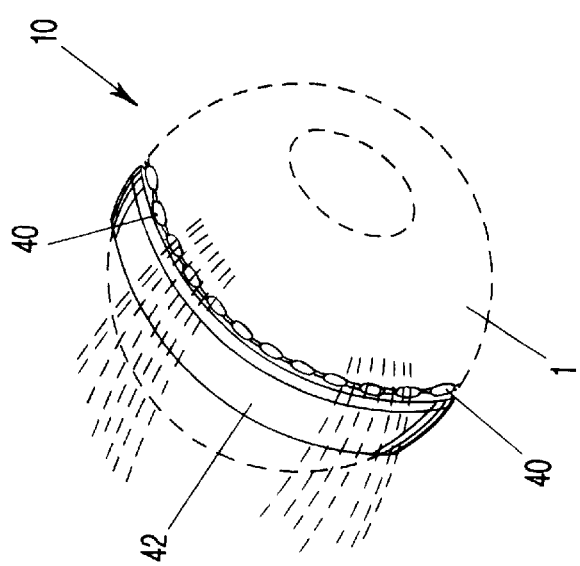
FIG. 5(a) is an isometric view of an alternate embodiment of the invention equipped with electroactive ionic polymeric sensors and actuator active bi-strip loops.

FIGS. 5(a), 5(b) and 5(c) show another embodiment of the invention equipped with electroactive ionic polymeric sensors and actuator bi-strips 40. FIG. 5(b) is a front view of the eye globe with sclera 10, bi-strip actuators 40 and an inextensible support band 42. FIG. 5(c) shows the ionic polymer active bi-strips equipped with an active polymer 44, induction coil 46, and end electrodes 48. Upon transcutaneous inductive powering of the bi-strip polymeric artificial muscle bi-strip actuators 40, embedded inside the smart band 3, active polymer bi-strips 44 expand outward and exert a constricting or squeezing circularly distributed force or pressure on the scleral tire 3, which in turn transmits that distributed annular force to the sclera 10, causing the axial length and local curvature of eye 1 to lengthen. This brings the retina/macula region to coincide with the focal point of the eye, and thus correct presbyopia.

Figures 6A, 6B:
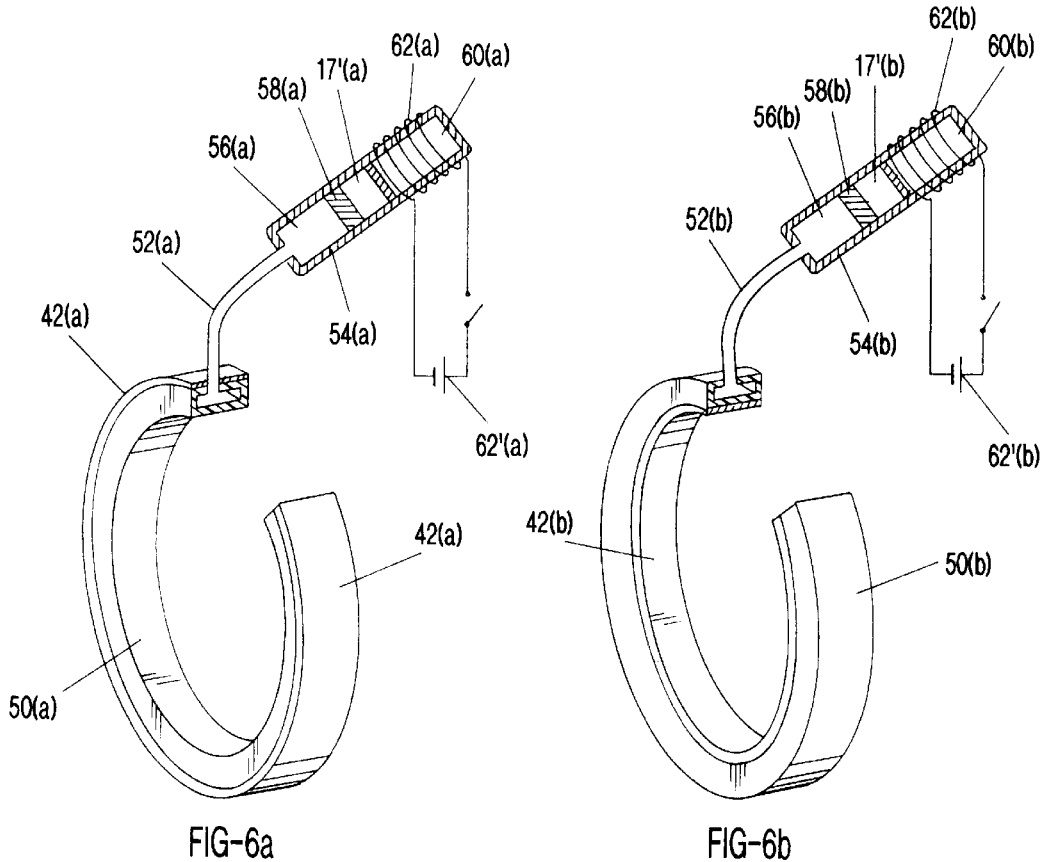
FIG. 6(a) is an isometric view of another alternate embodiment of the invention equipped with an inextensible outer support band and an inflatable inner bladder skirt for pneumatically squeezing the scleral globe to induce lengthening of the globe to correct hyperopia or presbyopia.
FIG. 6(b) is an isometric view of another alternate embodiment of the invention equipped with an elastic inner support band and an inflatable outer bladder skirt for pneumatically expanding the scleral globe to induce shortening of the globe to correct myopia.

FIG. 6(a) shows an isometric view of yet another embodiment of the invention. In this embodiment hydrogen gas is absorbed and desorbed using metal hydrides to cause a tightening and releasing of a band affixed to the scleral globe. The method for using metal hydrides in this fashion is described in Y. Wakisaka, et. al., Application of Hydrogen Absorbing Alloys to Medical & Rehabilitation Equipment, IEEE Trans. On Rehabilitation Engineering, vol. 5, no. 2, pp.

148–157, (1997). This embodiment comprises an inextensible support band 42(*a*) and an inflatable bladder skirt 50(*a*) for pneumatically squeezing the scleral globe 1 to induce lengthening of the globe. The inflation of the bladder 50(*a*) is created by a tube 52(*a*) attached to a cylinder 54(*a*) containing a source of bio-compatible gas, such as $CO_2$ or the like, in reservoir 56(*a*) to be pressurized by a piston 58(*a*) by means of a hydrogen gas 17'(*a*) which is desorbed from a metal hydride reservoir 60(*a*). The metal hydride reservoir 60(*a*) is transcutaneously and remotely inductively heated by an induction coil 62(*a*) and battery 62'(*a*) to cause hydrogen to desorb from it and push piston 58(*a*) to pressurize inner bladder 50(*a*) by the $CO_2$ gas in reservoir 60(*a*). The inflation of inner bladder 50(*a*) against the inextensible outer band 42(*a*), uniformly and circularly constricts the scleral tire 3 which in turn causes the eye length to increase and thus correct presbyopia and hyperopia by bringing the retina/macula region to coincide with the focal point of the eye.

FIG. 6(*b*) shows an isometric view of yet another embodiment of the invention similar to FIG. 6(*a*). In this embodiment hydrogen gas is absorbed and desorbed using metal hydrides to cause a tightening and releasing of a band affixed to the scleral globe. This embodiment comprises an elastic support band 42(*b*) and an inflatable outer bladder skirt 50(*b*) for pneumatically expanding the scleral globe 1 to induce shortening of the globe. The inflation of the bladder 50(*b*) is created by a tube 52(*b*) attached to a cylinder 54(*b*) containing a source of bio-compatible gas, such as $CO_2$ or the like, in reservoir 56(*b*) to be pressurized by a piston 58(*b*) by means of a hydrogen gas 17'(*b*) which is desorbed from a metal hydride reservoir 60(*b*). The metal hydride reservoir 60(*b*) is transcutaneously and remotely inductively heated by an induction coil 62(*b*) or a battery 62'(*a*) to cause hydrogen to desorb from it and push piston 58(*b*) to pressurize outer bladder 50(*b*) by the $CO_2$ gas in reservoir 60(*b*). The inflation of outer bladder 50(*b*) against the inextensible inner band 42(*b*), uniformly and circularly expands the scleral tire 3 which in turn causes the eye length to decrease and thus correct myopia by bringing the retina/macula region to coincide with the focal point of the eye.

Figures 7A, 7B:
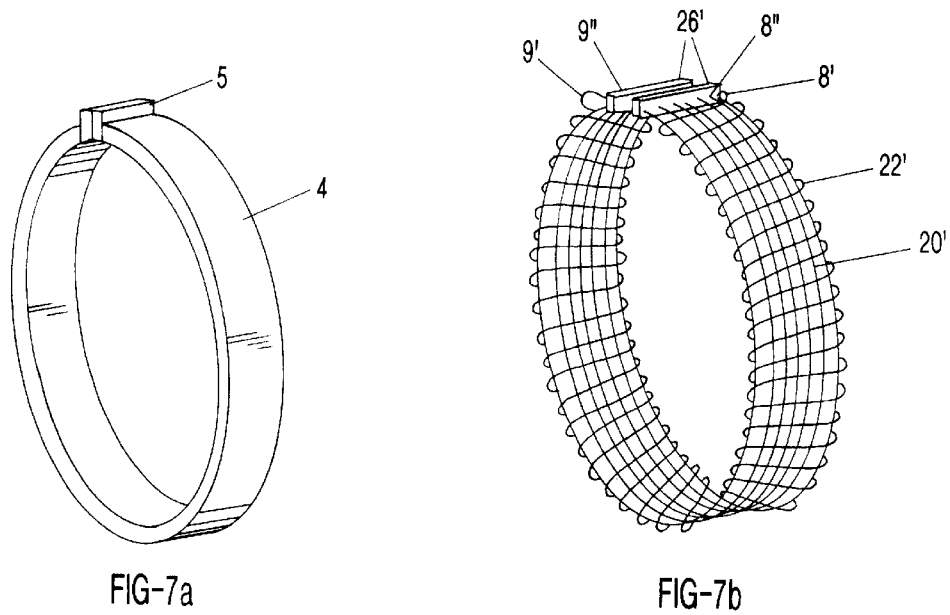
FIG. 7(a) is an isometric view of yet another alternate embodiment of the invention equipped with contractile electrically actuated polymeric or liquid crystal elastomeric fibers enclosed inside a silicone rubber cladding.
FIG. 7(b) is an isometric view of the liquid crystal elastomer wires enclosed inside an inductive heating coil similar to FIG. 2(b)

FIGS. 7(*a*) and 7(*b*) show another embodiment of the invention equipped with contractile electrically actuated polymeric or liquid crystal elastomeric fibers. FIG. 7(*a*) shows the prosthesis with silicone cladding 4 and snappable ends 5. FIG. 7(*b*) shows the embedded contractile liquid crystal elastomer (LCE) wires (ribbons) 20' and the induction coil 22' wrapped around the LCE wires (ribbons). The ends of the LCE wires (ribbons) 8' and 9' and their point of connections to the LCE wire assembly 8" and 9" and the end fixtures 26' to which the LCE wires or ribbons are bonded together. End fixtures 26' can be snapped or bonded together by standard means such as sutures, magnets, Velcro®, or the like. Referring to FIG. 2(*c*), note that induction generator 34, powered by a battery source E 30, and stabilized by a capacitor C 32, creates induction flux lines 11 to induce a current in the induction coil 22' of FIG. 7(*b*). Thus, one can remotely energize (heat) the LCE wires (ribbons) to an isotropicnematic phase transition temperature, of about 40 degrees Celsius, to cause the wires to contract and thus causing the prosthesis to uniformly and circularly constrict the sclera to cause an increase in the eye length and thus correct presbyopia and accommodate near object vision.

FIGS. 8(*a*) and 8(*b*) show an embodiment of the invention equipped with an inextensible support band or scleral tire 3 with snappable end fixtures 5 and an inflatable bladder skirt 50. To operate the apparatus, one pneumatically squeezes the scleral globe by means of a blow/suction tube 64 with a wider inlet 66 surgically implanted in the individual's nostrils as shown in FIG. (8*b*), to induce lengthening or shortening of the eye globe by means of the exhaled/inhaled $CO_2$ gas from the lungs.

FIGS. 9(*a*) and, 9(*b*), depict another embodiment of the present invention in which the constricting action is obtained by an endless solenoid or coil gun configuration composed of a telescopically constricting tubular band 70 with a golden armature winding 72 and a gold-plated hollow projectile 74. The operation of this embodiment, which will be placed in the groove or the tunnel of the scleral tire already described, is such that upon transcutaneous inductive powering of the electromagnetic coil 72, gold-plated projectile 74 will move in a direction to constrict or expand the band and make its inner diameter smaller or larger. Thus constricting or expanding effects are obtained to lengthen or shorten the eye and correct presbyopia, hyperopia or myopia on demand. FIG. 9(*a*) depicts an expanded configuration of the endless solenoid assembly, FIG. 9(*b*) depicts a constricted configuration of the endless solenoid assembly and powered by and inductive generator.

FIG. 10(*a*) shows a side view of another embodiment of the active scleral band of this invention wherein band 80 is comprised of a bio-compatible resilient polymer such as silicone with lockable male-female ends 86–88. The surgeon, in this case, fixably implants the band equatorially in the groove or the tunnel of the scleral tire which is already sutured to the sclera and adjusts the locking distance by choosing a certain insertion distance for the male-female locking ends 86 and 88. In doing so the surgeon pushes over the unlocking hole 82 in the transverse direction to allow for easy adjustment of the locking insertion distances.

FIG. 10(*b*) shows an isometric view of FIG. 10(*a*) and yet another embodiment of the active scleral band 80 of this invention wherein the band is comprised of a bio-compatible resilient polymer such as silicone with lockable male-female ends 86–88, unlocking hole 82 and pushing direction.

FIG. 11(*a*) shows an isometric view of yet another embodiment for myopes in the initial stage of operation (unsutured band) as a scleral expansion band 3 over the scleral globe 1 and under the extraocular muscles 2 to shorten the eye length to correct myopia in such a way that the retina/macula region is moved to coincide with focal point of the image 14.

FIG. 11(*b*) shows an isometric view of yet another embodiment for myopes in the final stage of operation (mattress sutured 6) as a scleral expansion band 3 over the scleral globe 1 and under the extraocular muscles 2 to shorten the eye length to correct myopia such that retina/macula region is moved to coincide with focal point of the image 14.

FIG. 11(*c*) shows a side view of the embodiment of FIG. 11(*b*) in the final stage of operation, showing the location of sutures 6, as a scleral expansion band 3 to shorten the eye length to correct myopia.

Figure 12B:
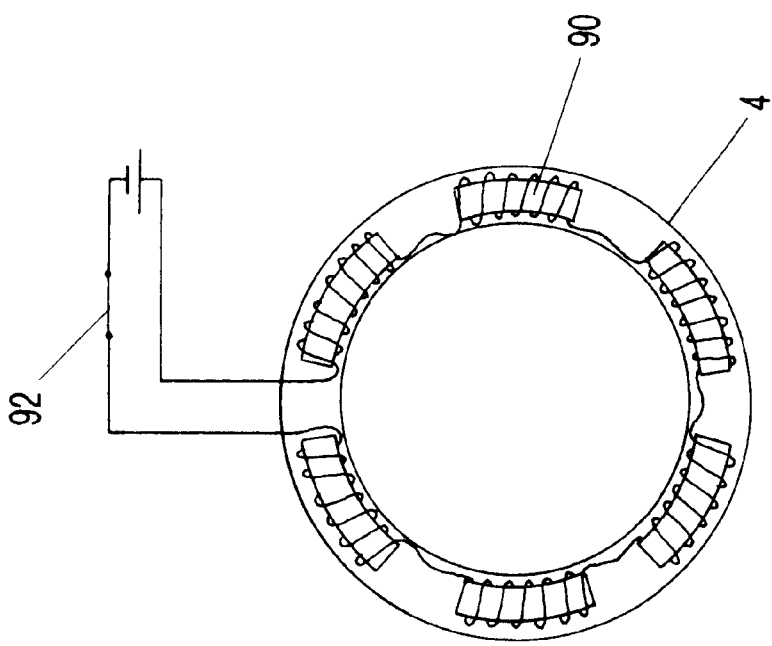
FIG. 12(b) depicts the same embodiment of FIG. 12(a) in an activated state.
Figure 12A:
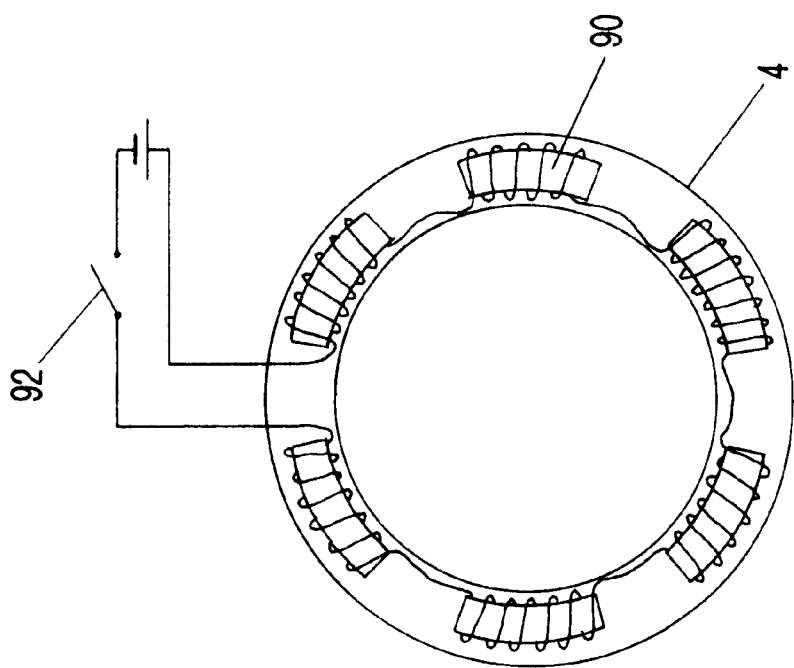
FIG. 12(a) depicts another embodiment of active constrictive band composed of silicone rubber cladding with embedded electro magnets in an inactivated state.

FIG. 12(*a*) is yet another embodiment of the active scleral band made with silicone rubber cladding 4 with embedded electro magnets 90 such that upon activation by switch 92 the active band constricts as shown in FIG. 12(*b*). Electro magnets 90 upon activation, attract each other thus shortening the circumference of the silicone rubber cladding 4. Upon deactivation, the elasticity of the silicone cladding 4 will expand the ring to its initial diameter.

To surgically implant any of the embodiments described herein, the preferred surgical procedure can be preformed.

Referring to FIG. 1(e), a 360-degree conjunctiva peritomy is performed. The conjunctiva is carefully dissected free from the sclera. Each of the extraocular muscles are isolated and freed from the check ligaments 2. A composite scleral band is placed underneath the extraocular muscles and secured together creating a 360 degree band encircling the sclera. The band is secured to the sclera by mattress sutures 6 using 6.0 nylon sutures, or the like.

In the alternative procedure, a 360-degree conjunctiva peritomy is performed. The conjunctiva is carefully dissected free from the sclera. An artificial muscle band is placed 3 mm from the sclera, preferably over ora serrata, and the band is sutured to ora serrata.

The procedures above are brief descriptions of the possible sites of implantation to induce length change by the constriction or expansion of the scleral buckle tire/artificial muscle structure smart band. The advantage of this technology is that it is an active mechanism to be implemented when one is reading. The Artificial Muscle will deactivate on command returning the axial length and scleral/corneal curvature to its original position.

Other patients that can use such active artificial muscle bands are cataract patients after replacement of their lens with intraocular lens (IOL). In these patients the ability to accommodate is again gone because the IOL is fairly inflexible and thus an active band will allow such patients to change their eye length and curvature to make accommodative corrections on demand. Finally, retinal detachment patients after surgery can use these bands for as long as it takes for their retina to reattach to scleral under the buckle pressure by healing. Once the detachment is repaired and healed the band can in fact be deactivated and the scleral buckle relaxed to enable the patients to go back to normal vision. Presently such patients suffer from induced unnecessary myopia due to the scleral buckle band constriction even after the detachment is healed. Thus an active scleral buckle band will correct this problem.

Although the invention has been described in detail with particular reference to these preferred embodiments, other embodiments can achieve the same results. Variations and modifications of the present invention will be obvious to those skilled in the art and it is intended to cover in the appended claims all such modifications and equivalents. The entire disclosures of all references, applications, patents, and publications cited above, are hereby incorporated by reference.

What is claimed is:

1. An apparatus for actively constricting and expanding the sclera of a human eye, the apparatus comprising:
    a band configured to be affixed around the sclera of the eye globe, said band comprising a means for actively constricting said band for increasing the axial length and local curvature of the eye globe and a means for actively expanding said band for decreasing the axial length and local curvature of the eye globe wherein said means for actively constricting and said means for actively expanding comprises a remotely controlled actuator.

2. The invention of claim 1 wherein said band comprises at least one composite artificial muscle.

3. The invention of claim 1 wherein said actuator comprises a heating apparatus to heat said at least one composite artificial muscle to an activation temperature.

4. The invention of claim 2 wherein said at least one composite artificial muscle comprises a shape memory alloy-silicone artificial muscle.

5. The invention of claim 2 wherein said at least one composite artificial muscle comprises an electroactive ionic polymeric artificial muscle.

6. The invention of claim 2 wherein said at least one composite artificial muscle comprises a thermally contractile liquid crystal elastomer artificial muscle.

7. The invention of claim 2 wherein said at least one composite artificial muscle comprises a mechanically contractile polymer artificial muscle.

8. The invention of claim 2 wherein said at least one composite artificial muscle comprises an electrically contractile polymer artificial muscle.

9. The invention of claim 2 wherein said at least one composite artificial muscle comprises a chemically contractile polymer artificial muscle.

10. The invention of claim 2 wherein said at least one composite artificial muscle comprises a magnetostrictive artificial muscle.

11. The invention of claim 1 wherein said band comprises a composite electromagnetic assembly and an electromagnetic actuator.

12. The invention of claim 11 wherein said composite electromagnetic assembly and electromagnetic actuator comprise a plurality of solenoids and linear motors.

13. The invention of claim 1 wherein said band comprises a silicone rubber band serially connected electromagnets.

14. The invention of claim 1 wherein said band comprises at least one inflatable bladder.

15. The invention of claim 14 wherein said at least one bladder is inflatable with a gas desorbed from a metal hydride source.

16. The invention of claim 15 further comprising a piston driven by said desorbed gas to inflate the said bladder with a biocompatible gas.

17. The invention of claim 14 wherein said at least one bladder further comprises at least one inlet tube for inflation and deflation of said at least one bladder.

18. The invention of claim 1 further comprising a connector for connecting a first end of said band to a second end of said band.

19. The invention of claim 18 wherein said connector further comprises an adjuster for circumferential adjustment of said band.

20. The invention of claim 1 wherein said band further comprises silicone cladding.

21. The invention of claim 1 wherein said band is configured to be affixed around the ora serrata.

* * * * *